(12) United States Patent
Kim et al.

(10) Patent No.: US 9,660,201 B2
(45) Date of Patent: May 23, 2017

(54) ORGANIC LIGHT EMITTING DEVICE

(71) Applicants:SAMSUNG DISPLAY CO., LTD., Yongin, Gyeonggi-Do (KR); PUSAN NATIONAL UNIVERSITY INDUSTRY—UNIVERSITY COOPERATION FOUNDATION, Busan (KR)

(72) Inventors: Mi Kyung Kim, Suwon-si (KR); Kwan Hee Lee, Suwon-si (KR); Chang Woong Chu, Hwaseong-si (KR); Jin Kook Lee, Busan (KR); Sam Il Kho, Seoul (KR)

(73) Assignees: Samsung Display Co., Ltd., Yongin-si (KR); Pusan National University Industry—University Cooperation Foundation, Busan (KR)

( * ) Notice: Subject to any disclaimer, the term of this patent is extended or adjusted under 35 U.S.C. 154(b) by 322 days.

(21) Appl. No.: 14/330,367

(22) Filed: Jul. 14, 2014

(65) Prior Publication Data

US 2015/0123087 A1    May 7, 2015

(30) Foreign Application Priority Data

Nov. 5, 2013   (KR) .......................... 10-2013-0133708

(51) Int. Cl.
*H01L 51/00*    (2006.01)
*C07D 209/86*   (2006.01)
(Continued)

(52) U.S. Cl.
CPC ........ *H01L 51/0072* (2013.01); *C07D 209/86* (2013.01); *C09B 26/02* (2013.01);
(Continued)

(58) Field of Classification Search
None
See application file for complete search history.

(56) References Cited

U.S. PATENT DOCUMENTS

2009/0134784 A1   5/2009   Lin et al.

FOREIGN PATENT DOCUMENTS

JP    2009-088538 A    4/2009
KR    10-2008-0044160 A    5/2008
(Continued)

OTHER PUBLICATIONS

Machine English translation of Iwakuma et al. (JP 2009-088538 A). Dec. 19, 2016.*

*Primary Examiner* — J. L. Yang
(74) *Attorney, Agent, or Firm* — Lewis Roca Rothgerber Christie LLP

(57) ABSTRACT

A compound for an organic light emitting device is represented by Chemical Formula 1. An organic light emitting device includes a first electrode, a second electrode facing the first electrode and an organic layer between the first electrode and the second electrode, and the organic layer includes a compound represented by Chemical Formula 1.

Chemical Formula 1

(Continued)

In the above Chemical Formula 1, Ar and L are the same as defined in the specification.

11 Claims, 1 Drawing Sheet

(51) Int. Cl.
*C09B 26/02* (2006.01)
*C09B 57/00* (2006.01)
*C09K 11/06* (2006.01)
*H01L 51/50* (2006.01)

(52) U.S. Cl.
CPC ............ *C09B 57/00* (2013.01); *C09B 57/008* (2013.01); *C09K 11/06* (2013.01); *C09K 2211/1007* (2013.01); *C09K 2211/1014* (2013.01); *C09K 2211/1029* (2013.01); *C09K 2211/1044* (2013.01); *H01L 51/0085* (2013.01); *H01L 51/5056* (2013.01); *H01L 51/5064* (2013.01)

(56) References Cited

FOREIGN PATENT DOCUMENTS

| KR | 10-2010-0099327 | 9/2010 |
|---|---|---|
| KR | 10-2011-0117513 | 10/2011 |

* cited by examiner

ORGANIC LIGHT EMITTING DEVICE

CROSS-REFERENCE TO RELATED APPLICATION

This application claims priority to and the benefit of Korean Patent Application No. 10-2013-0133708 filed in the Korean Intellectual Property Office on Nov. 5, 2013, the entire content of which is incorporated herein by reference.

BACKGROUND

1. Field

An organic light emitting device is disclosed.

2. Description of the Related Art

Since an organic light emitting device has light emitting characteristics and does not require a separate light source, unlike a liquid crystal display (LCD), the thickness and the weight of the organic light emitting device may be reduced compared to that of an LCD. And, since an organic light emitting device exhibits high definition characteristics such as low power consumption, high luminance and high response speed, and the like, it has been spotlighted as the next generation display device for portable electronic devices.

SUMMARY

Aspects of embodiments of the present invention are directed to an organic light emitting device having high efficiency and long life-span characteristics.

According to one embodiment, a compound for an organic light emitting device is represented by Chemical Formula 1.

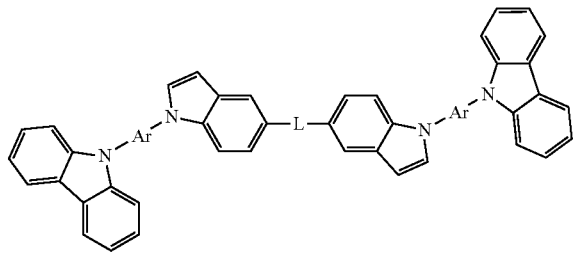

Chemical Formula 1

In the above Chemical Formula 1,

Ar is a substituted or unsubstituted C6 to C20 arylene group, a substituted or unsubstituted C2 to C20 heteroarylene group, or a combination thereof, and L is a single bond, a substituted or unsubstituted C6 to C10 arylene group, or a combination thereof.

The C6 to C20 arylene group may include a phenylene group, a naphthylene group, a biphenylene group, a terphenylene group, a phenanthrenylene group, or a combination thereof.

The C2 to C20 heteroarylene group may include nitrogen atom (N) as a ring atom.

The C2 to C20 heteroarylene group may include a pyridine group, a quinoline group, or a combination thereof.

According to another embodiment, an organic light emitting device includes a first electrode, a second electrode facing the first electrode and an organic layer between the first electrode and the second electrode, the organic layer including the compound represented by Chemical Formula 1.

The organic layer may be a single layer or a plurality of layers.

The organic layer may include a hole transport layer (HTL).

The organic layer may further include an electron transport layer (ETL).

The organic light emitting device including the compound for an organic light emitting device has high efficiency and long life-span characteristics.

DETAILED DESCRIPTION

Figure 1:
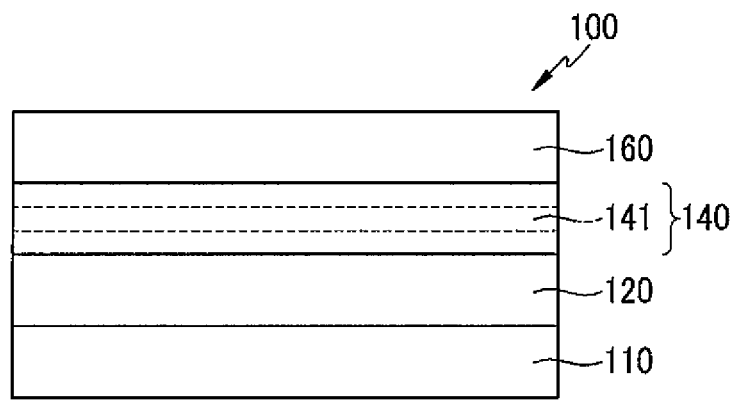
FIG. 1 is a schematic view of an organic light emitting device according to one embodiment.

Hereinafter, the present invention will be described with reference to the accompanying drawings, in which exemplary embodiments of the invention are shown. As those skilled in the art would realize, the described embodiments may be modified in various different ways, all without departing from the spirit or scope of the present invention, and should not be construed as being limited to the embodiments set forth herein.

Descriptions of parts not necessary for understanding the invention are omitted for clarity. Like reference numerals generally designate like elements throughout the specification.

The size and thickness of each constituent element as shown in the drawings were chosen arbitrarily for better understanding and ease of description, and this disclosure is not limited to the sizes and thicknesses chosen in the drawings.

In the drawings, the thickness of layers, films, panels, regions, etc., are exaggerated for clarity. In the drawings, the thicknesses of some layers and regions are exaggerated for better understanding and ease of description. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, the term "and/or" refers to at least one of the listed constituent elements. As used herein, constituent elements and/or portions are described using the words "first", "second", and the like, which are used for descriptive purposes only.

As used herein, when a definition is not otherwise provided, the term "substituted" may refer to a compound in which at least one hydrogen atom is substituted with a C1 to C30 alkyl group; a C1 to C10 alkylsilyl group; a C3 to C30 cycloalkyl group; a C6 to C30 aryl group; a C2 to C30 heteroaryl group; a C1 to C10 alkoxy group; a fluoro group, a C1 to C10 trifluoroalkyl group such as a trifluoromethyl group or the like; or a cyano group.

As used herein, when a definition is not otherwise provided, the prefix "hetero" may refer to a compound or a substituent including 1 to 3 heteroatoms selected from N, O, S, and P in the core structure, and carbon atoms as the remaining atoms in the core structure.

As used herein, when a definition is not otherwise provided, the term "combination thereof" refers to at least two substituents bound to each other by a linking group, or at least two substituents condensed with each other.

As used herein, when a definition is not otherwise provided, the term "alkyl group" may refer to a "saturated alkyl group" having no carbon-carbon double or triple bonds, or an "unsaturated alkyl group" including at least one of an alkenyl group or an alkynyl group. The term "alkenyl group" may refer to a substituent including at least one carbon-carbon double bond, and the term "alkynyl group" refers to a substituent including at least one carbon-carbon triple bond. The alkyl group may be a branched, linear, or cyclic alkyl group.

The alkyl group may be a C1 to C20 alkyl group, and in some embodiments a C1 to C6 alkyl group, a C1 to C4 alkyl group, a C7 to C10 alkyl group, or a C11 to C20 alkyl group.

For example, a C1 to C4 alkyl group may have 1 to 4 carbon atoms, and may be selected from methyl, ethyl, propyl, iso-propyl, n-butyl, iso-butyl, sec-butyl, or t-butyl.

Non-limiting examples of the alkyl group include a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, and the like.

The term "aromatic system" may refer to a compound including a cyclic structure where all ring atoms have p-orbitals which connect to form a conjugated system.

The term "aryl group" may refer to a monovalent carbocyclic aromatic system containing at least one ring. The term "arylene group" may refer to a divalent carbocyclic aromatic system containing at least one ring. The aryl group or the arylene group may be a monocyclic group containing one aromatic ring, or a polycyclic group containing at least two aromatic rings fused to each other (i.e., rings sharing at least one pair of carbon atoms).

The "heteroaryl group" may refer to a monovalent aromatic system containing at least one ring and including 1 to 3 ring heteroatoms selected from N, O, S, or P, and carbon atoms as remaining ring atoms. The "heteroarylene group" may refer to a divalent aromatic system containing at least one ring and including 1 to 3 ring heteroatoms selected from N, O, S, or P, and carbon atoms as remaining ring atoms. When the heteroaryl group or the heteroarylene group contains two or more rings, the two or more rings may be fused to each other, and each ring may include 1 to 3 ring heteroatoms selected from N, O, S, or P.

One embodiment of the present invention is directed to a compound for an organic light emitting device represented by the following Chemical Formula 1.

Chemical Formula 1

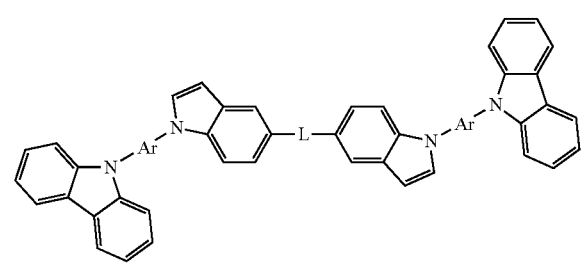

In the above Chemical Formula 1,

Ar is a substituted or unsubstituted C6 to C20 arylene group, a substituted or unsubstituted C2 to C20 heteroaryiene group, or a combination thereof, and L is a single bond, a substituted or unsubstituted C6 to C10 arylene group, or a combination thereof.

The compound represented by Chemical Formula 1 includes two indole groups in a core moiety and a carbazole group at each of the two terminal ends. The indole group and the carbazole group are linked to each other by an arylene group or a heteroarylene group represented by Ar.

The compound of Chemical Formula 1 includes two indole groups and two carbazole groups, which may be positioned to generally form a slightly asymmetric structure.

Non-limiting examples of the arylene group include a phenylene group, a naphthylene group, a biphenylene group, a terphenylene group, a phenanthrenylene group, or a combination thereof, but the arylene group is not limited thereto.

Non-limiting examples of the heteroarylene group include an arylene group in which 1 to 3 ring atoms are heteroatoms selected from N, O, S, and P, and in some embodiments, 1 or 2 ring atoms are heteroatoms.

For example, the heteroatom may be a nitrogen atom (N), but the heteroatom is not limited thereto. The heteroarylene group may be, for example, a pyridine group, a quinoline group, or a combination thereof, but the heteroarylene group is not limited thereto.

In one embodiment, the compound of Chemical Formula 1 may be used in an organic layer of an organic light emitting device. For example, the compound of Chemical Formula 1 may be used in the organic light-emitting device as a material for at least one layer selected from a hole injection layer (HIL), a hole transport layer (HTL), an electron blocking layer, an emission layer, a hole blocking layer, an electron transport layer (ETL), or an electron injection layer (EIL).

In one embodiment, the compound of Chemical Formula 1 may be used as a material for the hole transport layer (HTL). Since the compound of Chemical Formula 1 has a higher LUMO than the material generally used for a hole transport layer (HTL) of an organic light-emitting device, the compound of Chemical Formula 1 may block electrons and thus, may improve efficiency of the resulting organic light emitting device.

FIG. 1 is a schematic view of an organic light emitting device according to one embodiment. Referring to FIG. 1, an organic light emitting device 100 includes a first electrode 120, an organic layer 140 on the first electrode 120, and a second electrode 160 on the organic layer 140, all stacked on a substrate 110.

The substrate 110 may be a glass substrate, a silicon wafer, a polymer film, or the like.

One of the first electrode 120 and the second electrode 160 may be an anode and the other may be a cathode. The first electrode 120 and the second electrode 160 may each be a transparent or opaque electrode. For example, the first electrode 120 and the second electrode 160 may each include one selected from ITO, IZO, or a combination thereof, or one selected from aluminum (Al), silver (Ag), or a combination thereof.

In one embodiment, the organic layer 140 includes the compound represented by Chemical Formula 1 as described above.

The organic layer 140 may be a single layer or a plurality of layers. When the organic layer 140 is a single layer, the organic layer 140 may be a hole transport layer (HTL) 141. The hole transport layer (HTL) 141 may include the compound represented by the above Chemical Formula 1 and may have improved hole transport efficiency.

The organic layer 140 may further include an emission layer. The emission layer may be made of an organic material that emits light of a primary color such as red, green, blue, or the like, or may be a mixture of an inorganic material with the organic material such as, for example, a polyfluorene derivative, a (poly)paraphenylenevinylene derivative, a polyphenylene derivative, a polyfluorene derivative, a polyvinylcarbazole, a polythiophene derivative or a compound prepared by doping any one of these polymer materials with a perylene-based pigment, a coumarin-based pigment, a rhodamine-based pigment, rubrene, perylene, 9,10-diphenylanthracene, tetraphenylbutadiene, Nile red, coumarin, quinacridone, and the like. The resulting organic light emitting device may display a desirable image by displaying a combination of primary colors emitted by an emission layer therein.

The organic layer 140 may further include an auxiliary layer, in addition to the hole transport layer (HTL) described above. The auxiliary layer may include at least one layer selected from an electron transport layer (ETL), an electron injection layer (EL), a hole injection layer (HIL), or the like.

The organic light emitting device may realize low efficiency and long life-span characteristics and may be applied to top emitting devices, bottom emitting devices, top and bottom emitting devices, or the like, but the organic light emitting device is not limited to the specific embodiments herein.

Figure 2:
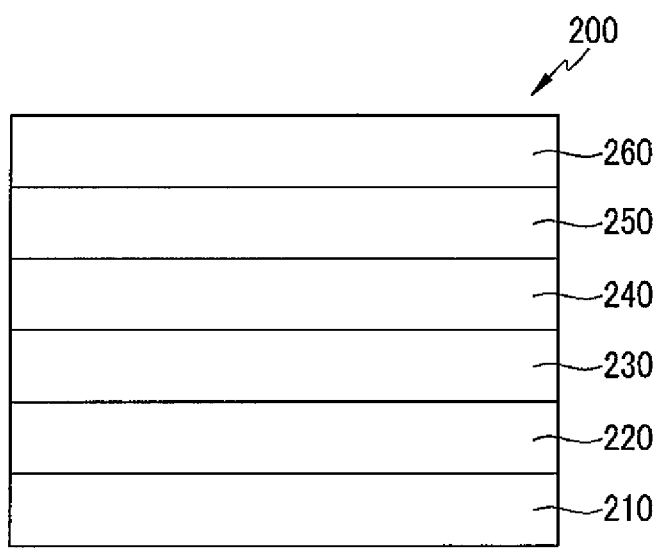
FIG. 2 is a schematic view of an organic light emitting device according to another embodiment.

FIG. 2 is a schematic view of an organic light emitting device according to another embodiment of the present invention.

Referring to FIG. 2, the organic light emitting device 200 includes a first electrode 220, a second electrode 260, and an organic emission layer 240 between the first electrode 220 and the second electrode 260, all stacked on a substrate 210. A lower auxiliary layer 230 may be between the first electrode 220 and the organic emission layer 240. An upper auxiliary layer 250 may be between the organic emission layer 240 and the second electrode 260.

The substrate 210, the first electrode 220, and the second electrode 260 are the same as described in FIG. 1.

The lower auxiliary layer 230, the organic emission layer 240, and the upper auxiliary layer 250 together may form the organic layer 140 of FIG. 1.

In one embodiment, one of the lower auxiliary layer 230 and the upper auxiliary layer 250 includes a hole injection layer (HIL) and/or a hole transport layer (HTL), and the other includes an electron transport layer (ETL) and/or an electron injection layer (EIL). For example, when the first electrode 220 is an anode and the second electrode 260 is a cathode, the lower auxiliary layer 230 includes a hole injection layer (HIL) and/or a hole transport layer (HTL), and the upper auxiliary layer 250 includes an electron injection layer (EIL) and/or an electron transport layer (ETL). In one embodiment, when the hole injection layer (HIL) and/or hole transport layer (HTL) are included in one auxiliary layer, the other auxiliary layer may be omitted.

In one embodiment, the organic emission layer 240 is the same as the emission layer described in connection with FIG. 1.

In one embodiment, the hole transport layer is the same as the hole transport layer described in connection with FIG. 1.

Hereinafter, the present disclosure is illustrated with reference to examples. However, these examples are exemplary, and the present disclosure is not limited thereto.

Synthesis of Compound for Organic Light Emitting Device

Synthesis Example 1

(1) Synthesis of Compound A 3.12 g (0.01 mol) of 4,4'-dibromo-biphenyl and 4.32 g (0.022 mol) of benzophenone hydrazone were dissolved in 60 mL of toluene, and 0.112 g (0.5 mol %) of Pd(OAc)$_2$, 0.26 g (0.55 mol) of tri-tert-butylphosphine, and 2.88 g (0.03 mol) of NaOtBu were added thereto. Then, the resulting mixture was refluxed and agitated under a nitrogen atmosphere for 36 hours. When the reaction was complete, methylene chloride was added to the reaction solution at room temperature, and the mixture was filtered with Celite and extracted three times with ethyl ether (10 mL). The obtained organic layer was collected and dried with magnesium sulfate, and the residue obtained by evaporating the solvent was separated and purified through silica gel column chromatography, thus obtaining 0.4382 g of Compound A as shown in the following Reaction Scheme A, as a white solid.

Compound A: $^1$H NMR (CD2Cl2, 400 MHz) δ (ppm): 7.51-7.62 (m, 8H), 7.45 (d, 4H), 7.26-7.33 (m, 10H), 7.10 (d, 4H)

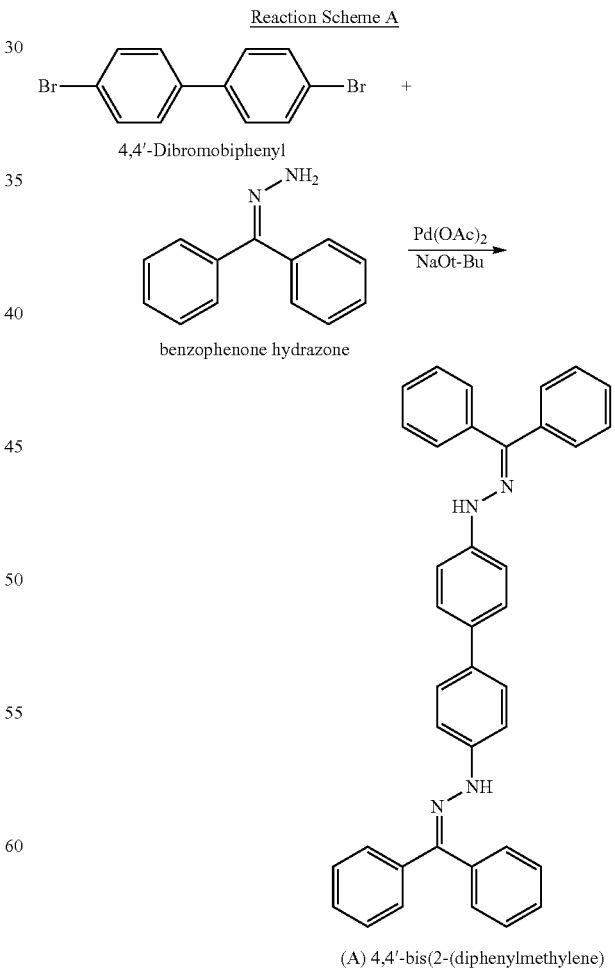

(A) 4,4'-bis(2-(diphenylmethylene)hydrazinyl)biphenyl

(2) Synthesis of Compound B 1.08 g (2.0 mmol) of Compound A and 1.52 g (8.0 mmol) of p-toluene sulfonic acid were added to 20 mL of methylethyl ketone, and the mixture was refluxed and agitated under a nitrogen atmosphere for 24 hours. When the reaction was complete, water was added thereto, and the resulting mixture was extracted three times with 20 mL of methylene chloride. The obtained organic layer was collected and dried with magnesium sulfate, and the residue obtained by evaporating the solvent was separated and purified through silica gel column chromatography, obtaining 0.34 g of Compound B as shown in the following Reaction Scheme B, as a light brown solid.

Compound B: $^1$H NMR (DMSO-d6, 200 MHz) δ (ppm): 11.4 (s, 2H), 7.21-7.43 (m, 6H), 2.35, (s, 3H), 2.28 (s, 3H)

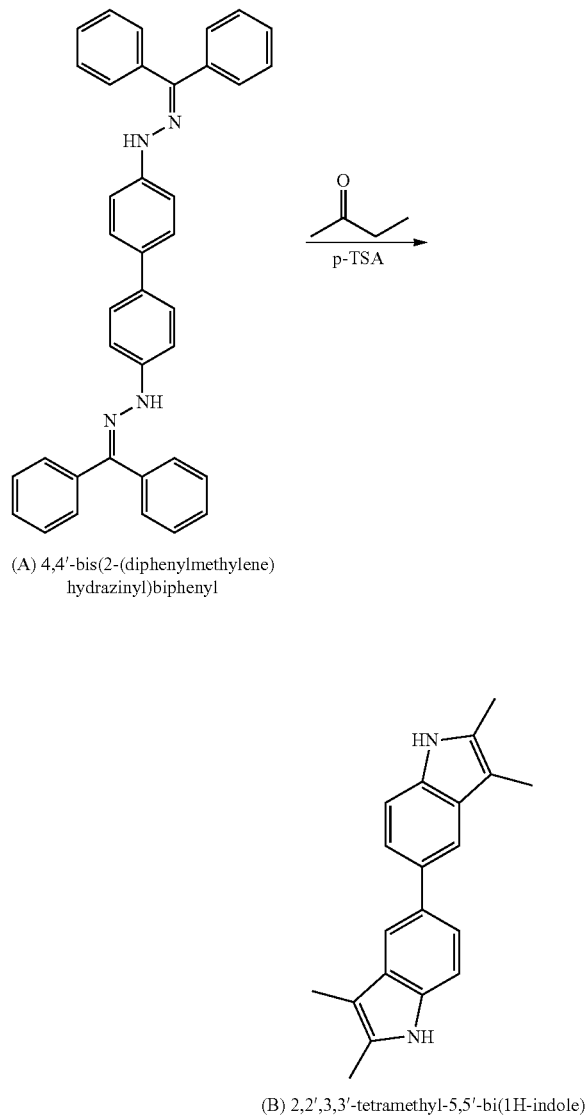

(A) 4,4'-bis(2-(diphenylmethylene)hydrazinyl)biphenyl (B) 2,2',3,3'-tetramethyl-5,5'-bi(1H-indole)

(3) Synthesis of Compound C 2.00 g (12.0 mmol) of 9H-carbazole and 3.08 g (13.1 mmol) of 1,4-dibromobenzene were added to 40 mL of DMF as a solvent. 4.16 g (30.20 mmol) of $K_2CO_3$, 0.46 g (2.40 mmol) of CuI, and 0.28 g (2.40 mmol) of L-proline as a catalyst or a ligand were added thereto, and the resulting mixture was refluxed and agitated under a nitrogen atmosphere for 24 hours. When the reaction was complete, the reactant was dissolved after removing the solvent by using an evaporating unit, and filtered through a silica gel pad. The obtained organic layer was collected and dried with magnesium sulfate, and the residue obtained by evaporating the solvent was separated and purified through silica gel column chromatography, obtaining 1.5 g of Compound C as shown in the following Reaction Scheme C.

Compound C: $^1$H NMR (CD2Cl2, 400 MHz) δ (ppm): 8.11-8.13 (d1, 2H), 7.70-7.81 (d2, 2H), 7.35-7.45 (m, 6H), 7.24-7.30 (d3, 2H)

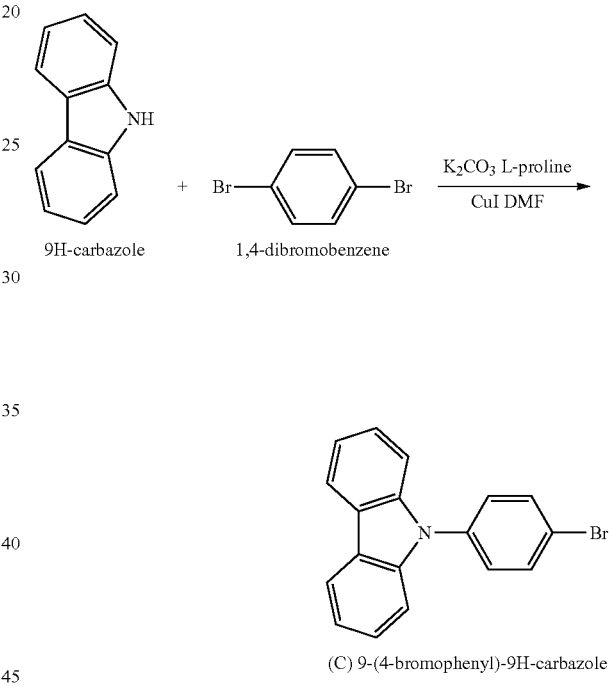

(C) 9-(4-bromophenyl)-9H-carbazole

(4) Synthesis of Compound D 0.60 g (2.08 mmol) of Compound B and 1.48 g (4.58 mmol) of Compound C were added to 10 mL of toluene. 0.60 g (6.24 mmol) of NaOt-Bu, 0.02 g (0.04 mmol) of 2-dicyclohexylphosphino-2',4',6'-triisopropylbiphenyl, and 0.04 g (0.04 mmol) of Pd(OAc)$_2$ as a catalyst or a ligand were added thereto, and the resulting mixture was refluxed and agitated under a nitrogen atmosphere for 15 hours at 120° C. When the reaction was complete, water was added thereto, and the resulting mixture was extracted three times with methylene chloride. The residue obtained by using an evaporating unit was separated and purified through silica gel column chromatography, obtaining 1.0 g of Compound D as shown in the following Reaction Scheme D.

Compound D: $^1$H NMR (CD2Cl2, 400 MHz) δ (ppm): 8.0 (d, 2H), 7.78-7.80 (d, 2H), 7.54-7.56 (m, 10H), 7.37-7.42 (m, 18H), 7.22-7.24 (d, 2H), 2.16 (s, 6H)

Reaction Scheme D

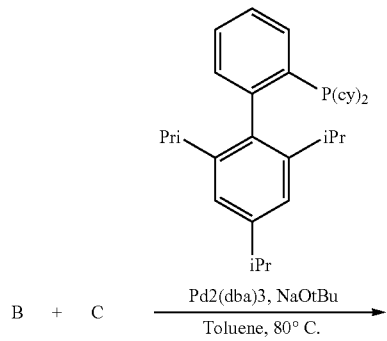

B + C  $\xrightarrow{\text{Pd2(dba)3, NaOtBu}}$  Toluene, 80° C.

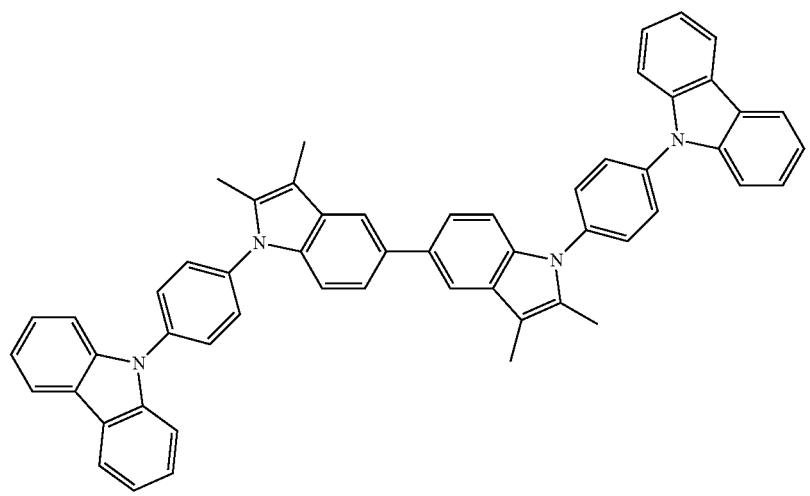

9,9'-((2,2',3,3'-tetramethyl-1H,1'H-[5,5'-biindole]-1,1'-diyl)bis(4,1-phenylene))bis(9H-carbazole)

Manufacture of Organic Light Emitting Device

Example 1

A 600 Å-thick hole injection layer (HIL) was formed by laminating and patterning ITO (an anode) on a glass substrate, and a 300 Å-thick hole transport layer (HTL) was subsequently formed by depositing Compound D from Synthesis Example 1 on the hole injection layer. Subsequently, a 200 Å-thick emission layer (EML) was formed on the hole transport layer. The 200 Å-thick emission layer was formed using alpha-ADN as the blue host and beta-ADN (BD1) represented by the following Chemical Formula aa as the dopant, where the dopant had a thickness of 3% based on the total 200 Å thickness of the emission layer. Subsequently, a 300 Å-thick electron transport layer (ETL) was formed by depositing ET1 represented by the following Chemical Formula bb on the emission layer. Subsequently, an electron injection layer (EIL) was formed on the electron transport layer by depositing lithium quinolate (Liq), and then a cathode was formed on the electron injection layer by depositing a 160 Å-thick layer of Mg:Ag (the Ag had a thickness of 10% based on the total thickness of the Mg:Ag layer).

Chemical Formula aa

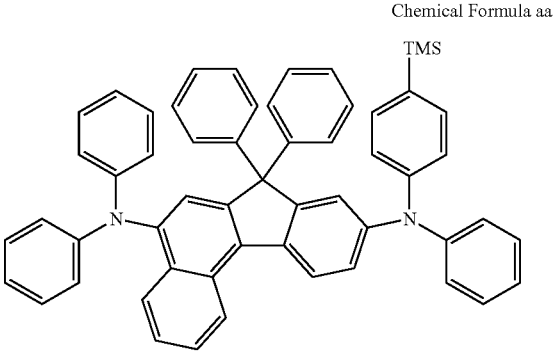

Chemical Formula bb

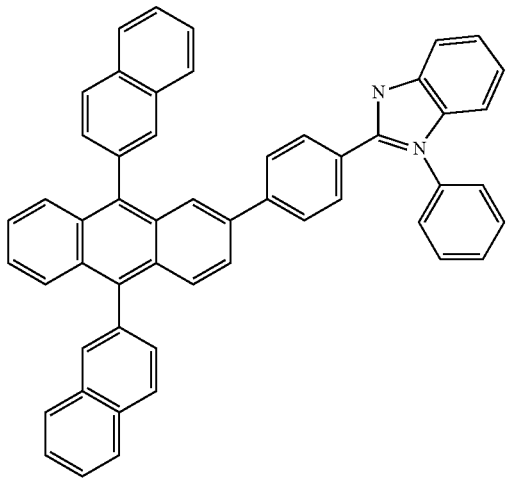

The manufactured organic light emitting device had the following structure. ITO/HIL/HTL(Compound D)/blue EML/ETL/EIL(Liq)/Mg:Ag Example 2

A hole injection layer (HIL) was formed by laminating and patterning ITO (anode) on a glass substrate. Then, a first hole transport layer (HTL1) was formed by depositing a compound represented by the following Chemical Formula cc on the hole injection layer (HIL), and a second hole transport layer (HTL2) was formed by depositing Compound D from Synthesis Example 1 on the first hole transport layer. Subsequently, a 400 Å-thick emission layer (EML) was formed on the second hole transport layer. The emission layer was formed by using PGH1 represented by the following Chemical Formula dd as a green phosphorescent host and Ir(ppy)3 as the dopant, where the dopant had a thickness of 15% based on the total thickness of 400 Å. Subsequently, a 300 Å-thick electron transport layer (ETL) was formed on the emission layer by depositing ET1 represented by the above Chemical Formula bb. Subsequently, an electron injection layer (EIL) was formed by depositing lithium quinolate (Liq) on the electron transport layer, and then a cathode was formed by depositing a 160 Å-thick layer of Mg:Ag (the Ag had a thickness of 10% based on the total thickness of the Mg:Ag layer).

Chemical Formula cc

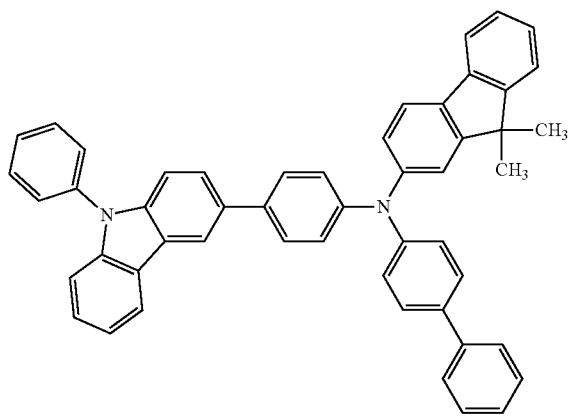

Chemical Formula dd

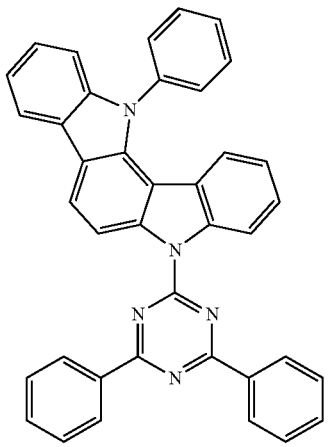

The manufactured organic light emitting device had a structure as follows. ITO/HIL/HTL1/HTL2 (Compound D)/green EML/ETL/EIL(Liq)/Mg:Ag Comparative Example 1

An organic light emitting device was manufactured as in Example 1 except for using N,N'-Di-[(1-naphthyl)-N,N'-diphenyl]-1,1'-biphenyl)-4,4'-diamine (NPB) instead of Compound D as the hole transport layer (HTL) material.

Comparative Example 2

An organic light emitting device was manufactured as in Example 2 except for using NPB instead of Compound D as the second hole transport layer (HTL2) material.

EVALUATION

Driving voltage, current density, current efficiency, and CIE color coordinates of the organic light emitting devices according to Examples 1 and 2 and Comparative Examples 1 and 2 were measured.

The results are provided in the following Table 1.

TABLE 1

| | Driving voltage (V) | Current density (mA/cm$^2$) | Current efficiency (cd/A) | Color coordinates | |
|---|---|---|---|---|---|
| | | | | CIE x | CIE y |
| Comparative Example 1 | 4.0 | 15.5 | 3.2 | 0.148 | 0.040 |
| Example 1 | 4.5 | 18.0 | 3.4 | 0.146 | 0.041 |
| Comparative Example 2 | 5.1 | 13.5 | 66.5 | 0.309 | 0.665 |
| Example 2 | 5.5 | 11.8 | 76 | 0.293 | 0.681 |

Referring to Table 1, the organic light emitting device according to Example 1 showed improved efficiency compared with the organic light emitting device according to Comparative Example 1, and the organic light emitting device according to Example 2 showed at least 10% improved efficiency compared with the organic light emitting device according to Comparative Example 2.

Without being bound by any particular theory, it is believed that the reason is that Compound D according to Synthesis Example 1 was included in the organic light emitting devices of Examples 1 and 2 and played a role of an electron barrier in the hole transport layer (HTL) and the second hole transport layer (HTL2), respectively, thus contributing to increased efficiency of the resulting organic light emitting device.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims and equivalents thereof.

What is claimed is:

1. A compound for an organic fight emitting device, the compound represented by Chemical Formula 1:

Chemical Formula 1

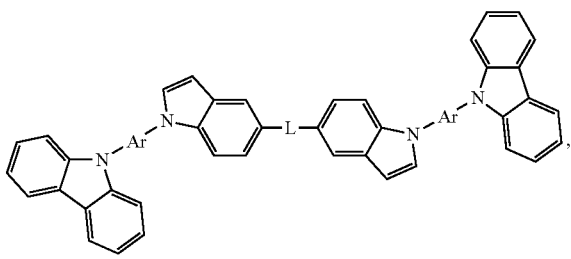

wherein,
Ar is a substituted or unsubstituted C6 to C20 arylene group, a substituted or unsubstituted C2 to C20 heteroarylene group, or a combination thereof, and
L is a single bond, a substituted or unsubstituted C6 to C10 arylene group, or a combination thereof.

2. The compound of claim 1, wherein the C6 to C20 arylene group comprises a phenylene group, a naphthylene group, a biphenylene group, a terphenylene group, a phenanthrenylene group, or a combination thereof.

3. The compound of claim 1, wherein the C2 to C20 heteroarylene group comprises a nitrogen atom (N) as a ring atom.

4. The compound of claim 3, wherein the C2 to C20 heteroarylene group comprises a pyridine group, a quinoline group, or a combination thereof.

5. An organic light emitting device comprising
a first electrode,
a second electrode facing the first electrode, and
an organic layer between the first electrode and the second electrode,
wherein the organic layer comprises a compound represented by Chemical Formula 1:

Chemical Formula 1

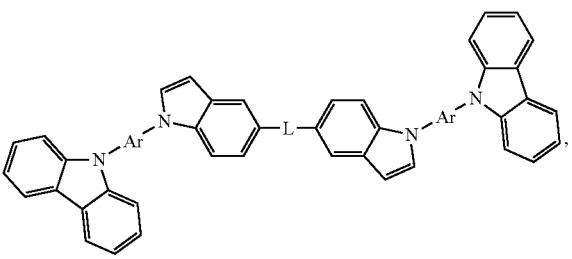

wherein,
Ar is a substituted or unsubstituted C6 to C20 arylene group, a substituted or unsubstituted C2 to C20 heteroarylene group, or a combination thereof, and
L is a single bond, a substituted or unsubstituted C6 to C10 arylene group, or a combination thereof.

6. The organic light emitting device of claim 5, wherein the C6 to C20 arylene group comprises a phenylene group, a naphthylene group, a biphenylene group, a terphenylene group, a fluorenylene group, or a combination thereof.

7. The organic light emitting device of claim 5, wherein the C2 to C20 heteroarylene group comprises a nitrogen atom (N) as a ring atom.

8. The organic light emitting device of claim 7, wherein the C2 to C20 heteroarylene group comprises a pyridine group, a quinoline group, or a combination thereof.

9. The organic light emitting device of claim 5, wherein the organic layer comprises a single layer or a plurality of layers.

10. The organic light emitting device of claim 5, wherein the organic layer comprises a hole transport layer.

11. The organic light emitting device of claim 10, wherein the organic layer further comprises an electron transport layer.

* * * * *